United States Patent [19]
Wong et al.

[11] Patent Number: 5,200,176
[45] Date of Patent: Apr. 6, 1993

[54] METHOD FOR PROTECTION OF ISCHEMIC TISSUES USING TUMOR NEROSIS FACTOR

[75] Inventors: Grace H. W. Wong, South San Francisco; David V. Goeddel, Hillsburough, both of Calif.

[73] Assignee: Genentech, Inc., South San Francisco, Calif.

[21] Appl. No.: 418,010

[22] Filed: Oct. 6, 1989

[51] Int. Cl.$^5$ .............................................. A61K 37/02
[52] U.S. Cl. ..................................... 424/85.1; 514/12; 530/351; 930/144
[58] Field of Search ....................... 530/351; 424/85.1; 514/12; 930/144

[56] References Cited

U.S. PATENT DOCUMENTS

| | | | |
|---|---|---|---|
| 4,808,402 | 2/1989 | Leibovich et al. | 424/423 |
| 4,846,782 | 7/1989 | Bonnem | 600/1 |
| 4,861,587 | 10/1989 | Urbascheb et al. | 424/85.1 |
| 4,985,241 | 1/1991 | Zimmerman et al. | 424/85.1 |

FOREIGN PATENT DOCUMENTS

| | | |
|---|---|---|
| 164965 | 12/1985 | European Pat. Off. |
| 168214 | 1/1986 | European Pat. Off. |
| 235906 | 9/1987 | European Pat. Off. |
| 239289 | 9/1987 | European Pat. Off. |
| 259863 | 3/1988 | European Pat. Off. |
| 284105 | 9/1988 | European Pat. Off. |
| 340005 | 11/1989 | European Pat. Off. |
| 357240 | 3/1990 | European Pat. Off. |
| WO91/15227 | 10/1991 | PCT Int'l Appl. |

OTHER PUBLICATIONS

Neta *J. Immunol* 140(1) 108–111 (1988).
Urbascheck et al. *Lymphokene Res.* 6(3) 179–186 (1987).
Neta *Blood* 72(3) 1093–1095 (1988).
Tsujimoto et al. *Biochem. Biophys. Res. Commun.* 137(3) 1094–1100 (1986).
Hellqvist et al., Dialog Information Services, file 155, Medline 66–91, Dialog accession No. 06998107.
Zimmerman et al., Dialog Information Services, file 155, Medline 66–91, Dialog accession No. 06866198.
Shalaby et al., *Leuk. Biol.* 41:196–204 (1987).
Wong, et al., *Science* 242:941–944 (1988).
Sugarman, B. J. et al., *Science* 230:943–945 (1985).
Carswell, E. A. et al., *Proc. Natl. Acad. Sci. USA*, 72:3666–3670 (1975).
Jacob, C. O. & McDevitt, H. O., *Nature*, 331:356–358 (1988).
Schütze et al., *J. Immunol.*, 140:3000–3005 (1988).
Maessen et al., *Transplantation Proc.*, 21(1):1261–1262 (1989).
Walton, P. E. & Cronin, M. J., *Endocrinology*, 125(2):925–929 (1989).
Gordon et al., *J. Appl. Physiol.*, 64:1688 (1988).
Sullivan et al., *Infection & Immunity*, 56(7):1722–1729 (1988).
Holtzmann et al., *J. Immunol* 139(4):1161–1167 (1987).
Cross et al., *J. Exper. Med.*, 169:2021–2027 (1989).
Wallach et a., *J. Immunol.*, 132:2464 (1984).
Hahn et al. *Proc. Natl. Acad. Sci. USA*, 82:3814 (1985).
Tiegs et al., *Biochem. Pharmacol.*, 38:627 (1989).
White et al., *J. Clin. Invest.*, 79:1868 (1987).
Urbaschek, et al, *Lymphokine Res.* 6(3):179–186 (1987).
Slordal, et al., *Eur J. Haematol* 43:428–434 (1989).
Neta et al., *Fed. Proc.* 46(4):1200 (abstract) (1987).
Neta et al., *J. Immunol.* 136(7):2483–2485 (1986).
Neta et al. *Pharmac. Ther.* 39:261–266 (1988).
Neta et al., *Lymphokine Res.* 5(1):S105–S110 (1986).

(List continued on next page.)

*Primary Examiner*—Garnette D. Draper
*Assistant Examiner*—Shelly J. Guest
*Attorney, Agent, or Firm*—Carolyn R. Adler

[57] ABSTRACT

Methods suitable for the protection, inhibition and prevention the deleterious effects of reactive oxygen species are provided, wherein an effective amount of a tumor necrosis factor is administered. Pretreatment of tissues and organs to be transplanted is described. Perfusion solutions and the preparation of perfused, excised tissue are described.

21 Claims, 2 Drawing Sheets

OTHER PUBLICATIONS

Clark, A. and Chaudhri, G., *J. of Cellular Biochem., UCLA Symposia on Molecular and Cellular Biology*, Supplement 12a:B023 (1988).

Matsubara et al., *J. Immunol.* 137:3295–3298 (1986).

Leurs et al., *Biochemistry International* 18(2):295–299 (1989).

Hjalmarsson et al., *Proc. Natl. Acad. Sci. USA* 84:6340 (1987).

Saez et al., *Proc. Natl. Acad. Sci. USA*, 84:3056 (1987).

Oda et al., *Science* 244:974–976 (1989).

Omar et al., *Cancer Res.* 47:3473 (1987).

Taylor et al., *Brain Res.*, 347:268 (1985).

Braquet et al., *Int. Arch. Allergy Appl. Immunol.* 88:88–100 (1989).

Galaris et al., *Biochem. Biophys. Res. Comm.*, 160(3):1162–1168 (1989).

Kalayoglu et al., *The Lancet*, Mar. 19, 1988, pp. 617–619.

Palladino et al., *Int. J. Radiat Biol.*, 41:183–91 (1982).

Omar, B. A. and McCord, J. M., *Free Radical Biology & Medicine*, 9:473–478 (1990).

Omar, B. A. et al., *Free Radical Biology & Medicine*, 9:465–471 (1990).

Decker, T. and Lohmann-Matthes, M-L., *J. of Immunol. Methods*, 15:61–69 (1988).

Berkow et al. *J. Immunol* 139(11)3783–3791 (1987).

TNF-α:   −  +      −  +

MnSOD 4kb

MnSOD 1kb

METHOD FOR PROTECTION OF ISCHEMIC TISSUES USING TUMOR NEROSIS FACTOR

BACKGROUND OF THE INVENTION

This invention relates to methods for inhibiting, preventing, protecting against or treating the deleterious effects of reactive oxygen species. The invention also relates to methods for protecting against injury to tissues from ischemia and reperfusion injury.

Superoxide radicals ($O_2^-$) and other highly reactive oxygen species such as hydrogen peroxide ($H_2O_2$) and hydroxyl radicals (referred to herein as reactive oxygen species or "ROS") are produced in vivo by enzymatic, spontaneous, and photochemical oxidation reactions. ROS are produced by mitochondria during electron transport. Other intracellular sources of $O_2^-$ and $H_2O_2$ are endoplasmic reticulum, peroxisomes, and nuclear and plasma membranes. Examples of disorders associated with the generation of ROS include: synovial inflammation induced by bacterial lipopolysaccharide endotoxin (LPS), inflammation caused by adjuvant-induced arthritis, bleomycin-induced lung fibrosis, reperfusion injury, transplantation rejection, hyperoxia, and any diseases caused by light. It has been suggested that ROS may be involved in hyperthermic cell injury (Omar et al., Cancer Res. 47:3473, 1987), and that thermosensitivity is linked to a low rate of free radical removal.

Certain agents are capable of inducing superoxide or other oxygen free radicals. Such ROS activity may be determined by commonly used methods, such as their ability to induce guinea pig alveolar macrophages to produce reactive oxygen metabolites which are measurable by spectrometer at $A_{550-540nm}$ (Leurs at al., Biochemistry International 18 (2):295-299, 1989), or by known inflammatory or chemiluminescence test models. Agents which are known to enhance the production of ROS include but are not limited to the following commercially available compounds: inhibitors of glutathione synthesis such as buthionine sulfoximine, anthracyclines such as adriamycin (doxorubicin), adriamycinone (doxorubicinone), daunomycin, daunomycinone, daunorubicin, and daunorubicin derivatives such as 5-iminodaunorubicin, ubiquinone, Acid Blues 25, 80, and 41, Acid Green 25, anthraquinone and its derivatives such as 2-bromoanthraquine, 1,2-dihydroxyanthraquinone, 1,8-diaminoanthraquinone, 2,6-diaminoanthraquinone, 1,5-dichloroanthraquinone, 1,2-diaminoanthraquinone, and 2-chloro-anthraquinone, quinizarin, anthrarufin, quilalizarin, aloe-emodin and related compounds such as 5-nitro-aloe-emodin, 5-amino-aloe-emodin, 2-allylaloe-emodin, averufin, kalafungin, alizarin complexone dihydrate, quercetin dihydrate, acid black 48, procytoxid, leucotrofina, azimexon, and methoxycin-namonitrile. These ROS inducing agents may be administered therapeutically, by intravenous or other methods as desired.

A group of metalloproteins known as superoxide dismutases (SOD) catalyze the oxidation-reduction reaction $2O_2^- + 2H^+ \rightarrow H_2O_2 + O_2$ and thus provide part of the defense mechanism against oxygen toxicity. Eukaryotic cells contain copper-zinc SOD, which is found predominantly in the cytosol, and MnSOD, which is found mainly in mitochondria. Extracellular SOD is found primarily in extracellular fluids such as plasma, lymph, and synovial fluid, but occurs also in tissues (Hjalmarsson et al., Proc. Natl. Acad. Sci. USA 84:6340, 1987).

The scientific literature suggests that SOD administration may be useful in a wide range of clinical applications. Potential applications include prevention of oncogenesis and of tumor promotion, treatment of inflammations, reduction of the cytotoxic and cardiotoxic effects of anticancer drugs, protection of ischemic tissues and protection of spermatozoa (EPO Appl. EP 0 284 105 A2). It has also been suggested that oxygen free radicals are involved in the pathogenesis of, and that SOD administration protects against, influenza virus infection (Oda et al., Science 244: 974-976, 1989).

Ischemia causes injury to cells, and if continued for a sufficient length of time, can kill them. Reperfusion after a brief period of ischemia, although beneficial in the long term, frequently results in an initial injury to the tissues upon reoxygenation, presumably through the formation and involvement of reactive oxygen species. This phenomenon has been described in the literature with heart, skin, intestine, pancreas, and variety of tissues. It is also important to protect against reoxygenation injury during thrombolytic therapy, and in the preservation of organs for transplantation.

Tumor necrosis factors (TNFs) are polypeptides produced by mitogen-stimulated macrophages (TNF-$\alpha$) or lymphocytes (TNF-$\beta$) which are cytotoxic to certain malignantly transformed cells but not to certain normal cells (E. A. Carswell et al., Proc. Natl. Acad. Sci. U.S.A. 72:3666, 1975; B. J. Sugarman et al., Science 230:943, 1985; Schutze et al., J. Immunol. 140: 3000, 1988). TNF-$\alpha$ has been suggested to be responsible for wasting and cachexia in patients with cancer or severe infections, and both TNF-$\alpha$ and TNF-$\beta$ mediate many other biological effects. TNF is also known to induce MHC antigens. The inventors herein have reported that TNF induces MnSOD in various transformed and normal cell lines (Wong et al., Science 242:941, 1988).

TNF at certain dosages is known to trigger the generation of ROS in macrophages or neutrophils (Tsujimoto et al., Biochem. Biophys. Res. Commun. 137:1094, 1986; Matsubara et al., J. Immunol. 137:3295, 1986; Shalaby et al., Leuk. Biol. 41:196, 1987; Berkow et al., J. Immunol. 139:3783, 1987). It has been suggested repeatedly in the literature that TNF at certain dosages enhances tissue injury caused by reactive oxygen species (see, e.g. Clark et al., J. Cell Biochem. Suppl. 12A, p. 40, Jan 1988; Sullivan at al., Infect. and Immunity 56(7): 1722-1729, 1988; and Tiegs at al., Biochem. Pharmacol. 38(4): 627-631, 1989).

The literature has reported that TNF-$\alpha$ and other cytokines such as IL-1 may protect against the deleterious effects of ionizing radiation produced during a course of radiotherapy, such as denaturation of enzymes, lipid peroxidation, and DNA damage (Neta et al., J. Immunol. 136(7):2483, 1987; Neta et al., Lymphokine Res. 5(1):5105-110 (1986) Neta et al., Fed. Proc. 46:1200 (abstract), 1987; Urbaschek et al., Lymphokine Res. 6:179, 1987; U.S. Pat. No. 4,861,587; Neta et al., J. Immunol. 140:108, 1988), and that TNF treatment accelerates restoration of hematopoiesis in animals compromised by sublethal doses of cytotoxic drugs or irradiation (Neta, et al., Blood 72(3):1093, 1988). A recent article reported that pretreatment with TNF protects mice from lethal bacterial infection (Cross et al., J. Exp. Med. 169:2021-2027, 1989). It has also been suggested that administration of subdeleterious amounts of TNF and/or IL-1 may modulate the deleterious effect of subsequent TNF and/or IL-1 administration; this reference further suggests that ionizing radiation may be administered as a sensitizing agent (EPO Appl. EP 0 259 863 A2). It has also been reported that pretreatment of cells with low levels of either TNF or IL-1 can confer resistance to killing by subsequent treatment with TNF-α and cycloheximide in combination (Wallach, J. Immunol. 132:2464, 1984; Hahn et al., Proc. Natl. Acad. Sci. U.S.A. 82:3814, 1985; Holtmann et al., J. Immunol 139:1161, 1987). It has been suggested that inadequate endogenous levels of TNF may be involved in the development of lupus erythematosus (Jacob et al., Nature 331:356–358, 1988).

It is an object of this invention to provide methods for protecting ischemic tissues, such as those tissues, bones or organs to be transplanted from a donor to a recipient patient, or those tissues whose oxygen supply has been blocked, from the effects of ROS.

It is a further object herein to provide methods to inhibit, prevent or treat reperfusion injury, bronchopulmonary dysplasia, stroke, arteriolosclerosis, atherosclerosis, myocardial infarct, inflammatory autoimmune diseases, viral infection, inflammation-induced arthritis, hyperoxia, sepsis, diabetes, influenza, multiple sclerosis, premature birth, acquired immunodeficiency syndrome, transplant rejection or transplantation injury, bleomycin-induced lung fibrosis, synovial inflammation induced by bacterial LPS endotoxin, lung injury resulting from immune complexes, kidney disease, Parkinson's disease, sickle cell anemia, sickle cell trait, alcoholic or non-alcoholic cirrhosis, or other diseases associated with toxic ROS.

Another object of this invention is to supply perfusion solutions and excised, perfused tissues for transplant.

These and other objects of the invention will be apparent from consideration of the specification as a whole.

SUMMARY OF THE INVENTION

Unexpectedly, and contrary to the suggestions in the literature, the present inventors have discovered that pretreatment with certain doses of TNF protects against ROS damage.

The objects of this invention are accomplished by methods utilizing this effect of TNF. In one preferred method, a patient at risk for reperfusion injury is treated with an effective but sub-deleterious amount of a TNF before, at, or after, but preferably prior to reperfusion. In another embodiment, a patient with a condition or disease associated with ROS (as described above) is treated with a dose of TNF which is effective at preventing, inhibiting or treating that condition.

Other preferred embodiments relate to tissue transplant. In one embodiment, ischemic tissue is protected by the administration of an effective amount of a TNF prior to reperfusion of the tissue. This ischemic tissue may be treated prior to or after removal from a donor, and before or after it is transferred to or implanted in a recipient patient.

This invention also encompasses perfusion solutions comprising TNF in a pharmaceutically acceptable excipient, as well as perfused, excised tissues, where the tissues are perfused with such a perfusion solution.

In an alternate embodiment, TNF is administered to a tissue donor prior to preparation for removal of the tissue.

DETAILED DESCRIPTION

Figure 1:
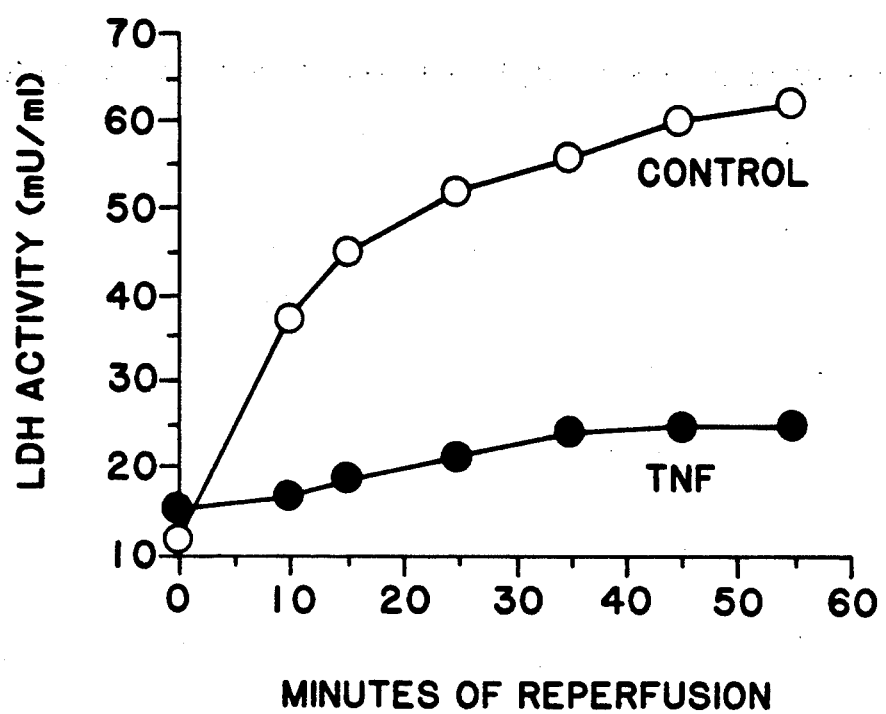
FIG. 1 shows that TNF pretreatment protects against heart damage due to ischemia and reperfusion.

Tumor necrosis factor or TNF, as employed herein, refers in general to the various forms of TNF which exhibit one or more biologic properties of tumor necrosis such as tumor cell lysis, inhibition of infectious agents, class II antigen induction, and neutralization by antibody to TNF-α or TNF-β but not by antibodies to other cytokines. It is believed that gamma interferon is synergistic with TNF in anti-tumor or anti-viral assays for TNF, and may therefore be desirably administered along with TNF in the practice of this invention.

In particular, the tumor necrosis factors useful herein include TNF-α and TNF-β. The former is described in copending EPO Appl. EP 0 168 214 A2 together with methods for its synthesis in recombinant cell culture. Similarly, the latter (previously called lymphotoxin) and suitable recombinant synthesis methods are described in copending EPO Appl. EP 0 164 965 A2. The TNF-α and TNF-β described in these applications include cytotoxic amino acid sequence and glycosylation variants which also are used herein. Of course, TNF-α or TNF-β from non-recombinant sources are also useful in the practice of this invention.

TNF-α or TNF-β are used alone or in admixture with one another in proportions empirically determined to exert the most effective clinical response. TNF is not species specific, so TNFs from other animal species. e.g. porcine or bovine, are useful for treatment of humans. The preferred TNF for treatment of humans is mature human TNF-α from recombinant microbial cell culture. The TNF ordinarily will have a cytolytic activity on susceptible L-929 murine cells of greater than about $1 \times 10^6$ units/mg, wherein a unit is defined as set forth in the above-described patent applications, the disclosures of which are incorporated by reference.

The formulations may contain compounds previously suggested for use in the treatment of the conditions and diseases described herein, as well as those compounds previously suggested for use in preventing damage from ROS. Antioxidants, such as ascorbate, fibrinolytic agents such as tissue plasminogen activator, and other compounds previously suggested for use in preventing reperfusion injury may also be included. Agents that block the toxicity of high doses of TNF--such as glucocorticoids and indomethacin--without altering the MnSOD-inducing activity of TNF--are also utilized in the practice of this invention. Agents which block induction of MHC antigens are also desirably administered with TNF. Compounds which effect the redox potential of ROS may also be utilized in a formulation. TNF also is suitably formulated together with known agents in order to modify or enhance the half-life or therapeutic activity of the TNF. These other agents or therapies are used at the same time as TNF is administered or in a sequential course of therapy.

TNF is placed into sterile, isotonic formulations together with required cofactors. The formulation of TNF is preferably liquid, and is ordinarily a physiologic salt solution or dextrose solution, together with conventional stabilizers and/or incipients. The composition may also be provided as lyophilized powder for ultimate delivery in solution. Saline is a suitable carrier, although other conventional parenteral solutions or buffers are usable.

Figure 2:
FIG. 2 shows two experiments indicating the induction of MnSOD RNA in ischemic rat hearts pretreated with TNF prior to reperfusion.
Figure 2:

In a pharmacologic sense, in the context of the present invention, a therapeutically effective amount of TNF refers to that amount effective to protect normal cells from the deleterious effects of ROS. Although it is currently believed that induction of MnSOD is not sufficient to protect cells from damage, monitoring of its induction by TNF is a convenient indication of TNF activity under this invention. As shown in FIG. 2, TNF induces MnSOD in ischemic rat hearts pretreated with TNF before reperfusion.

The therapeutically effective dosage of TNF to be administered to a human patient or human tissue generally will range from about 1-250 $\mu g/m^2$ per dose, and preferably from about 1-10 $\mu g/m^2$, and most preferably 10 $\mu g/m^2$, although the dose of the TNF administered will be dependent upon the species of the patient, the properties of the TNF employed, e.g. its activity and biological half-life, the concentration of the TNF in the formulation, the rate of dosage, the clinical tolerance of the patients involved, the pathological condition of the patients and the like, as is well within the skill of the physician. It will be appreciated that the practitioner will adjust the therapeutic dose in line with clinical experience for any given TNF. Preferably, the TNF is administered intravenously or intramuscularly.

In the practice of this invention, compositions which include a therapeutically effective amount of TNF are administered to patients having or at risk for damage from ROS. Accordingly, in some embodiments of this invention, the TNF, alone or with other agents as described above, is administered to a patient within a temporal period, most preferably within 24 hours prior, preferably prior to or concurrent with, or shortly following exposure, to ROS. In the case of reperfusion, exposure to the ROS may be predetermined and deliberate, or may be a consequence of other therapeutic measures.

In other embodiments, a patient's ROS exposure is of a more chronic or regular nature, as with certain of the diseases and chronic conditions described above. In these situations, TNF may be administered as part of a long-term course of therapy.

Some embodiments deal with the transfer to and implantation of tissues, and the complex tissues known as organs, in a recipient patient. For purposes of this invention, the term "tissues" shall be understood to include, without limitation, muscle tissue, connective tissue, epithelial tissue, nervous tissue, vascular tissue, bone, brain, reproductive organs, respiratory organs, digestive organs, excretory organs, urinary organs, sensory organs, and skeletal muscle organs. Particularly preferred tissues include heart, lung, kidney, liver, skin and bone grafts. Suitable tissues are synthetic as well as those which are removed from a donor.

For tissues to be removed from a donor prior to their transfer to and implantation in a patient, treatment with TNF may be accomplished in several different ways. TNF may be administered to the donor, as described above. Alternatively, the tissue itself may be treated, either prior to or after removal from the donor, and either prior to or after transfer to the patient, but most preferably prior to or concurrent with reperfusion.

Since the first successful human orthotopic liver transplant by Starzl in 1967, methods for the transplant of tissues, as well as suitable protocols for their perfusion with various agents, have become commonly known in the art. Suitable protocols and perfusion solutions are described, for example, in Kalayoglu et al., The Lancet, Mar. 19, 1988, pp. 617-619. Perfusion is commonly accomplished with a mechanical pump, as described in Example 1 below. Suitable perfusion solutions include lactated Ringer's solution, UW solution, and pharmaceutically acceptable isotonic solutions. These solutions enable a TNF-treated tissue to be preserved by continuous perfusion or cold storage until it is implanted into a recipient patient.

In an embodiment of this invention, perfusion solutions are provided, comprising TNF at a concentration of approximately 1-250 $\mu g/m^2$ with a pharmaceutically acceptable isotonic solution.

For each type of disease or injury, and for each animal species to be treated, the exact TNF dosage necessary for this protective effect may vary from that shown herein, and the exact administration parameters suitable for any given patient or animal species will be determined by routine experimentation. Typically, the patient or tissue is first administered TNF, e.g. by intravenous or intramuscular administration, and thereafter exposed to ROS. The patient or tissue is monitored for symptoms of any beneficial or deleterious effects of the treatment. If the initial treatment is partially successful or unsuccessful, the process may be repeated, optionally with modification of the dosage or route of administration.

According to this invention, patients from differing species are all treated by the pharmaceutically acceptable administration of TNF in a pharmaceutically effective dosage and for a period of time sufficient to inhibit, prevent, protect from the damaging effects of ROS.

It is also envisioned that, in the practice of this invention, administration of TNF may be accompanied by the therapeutic administration of a course of radiation, heat, and/or ROS inducing agents. The TNF, alone or with other agents, may be administered to a patient prior to, following, or simultaneously with exposure to radiation, heat, or ROS inducing agents. Exposure to the radiation, heat, or ROS inducing agents may be predetermined and deliberate, or may be a consequence of other therapeutic measures. Heat or ROS-inducing agents may be administering with radiation, and/or with an additional dose of TNF.

ROS inducing agents and their methods of administration are described above. Radiation and heat are administered by protocols commonly known to practitioners, as described in the literature cited above. Typically, radiation is given in pulses over a period of time from 1-8 weeks, for a total dose of approximately 1000-1200 rads. Heat may be administered by known methods such as a heat blanket or hyperthermia chamber, for a period sufficient to raise a patient's body tissue temperature about 37° C., preferably 40°-45° C., and most preferably to approximately 42° C.

In order that the invention described herein may be more fully understood, the following example is set forth. It should be understood that this example is for illustrative purposes only, and is not to be construed as limiting this invention in any manner.

EXAMPLE

The Effect of TNF on Isolated Rat Heart

Healthy Sprague Dawley rats weighing between 200 and 300 g are anesthetized with sodium pentobarbital, 30 mg/kg, intraperitoneally. Heparin (500 U) is administered intravenously. The chests are opened and the hearts rapidly excised and placed in iced cold buffer until they stop beating. The hearts are mounted by the aortic roots to a stainless steel cannula and perfused through the aorta in a retrograde manner (Langendorff). Krebs-Henseleit buffer of the following composition is used throughout the experiments (final concentration in mM/L): NaCl, 118; KCl, 4.7; CaCl, 2.5; MgSO, 1.2; KH PO, 1.2; CaEDTA, 0.5; NaHCO, 25; and glucose, 10. The buffer is aerated with 95% $O_2$–5% $CO_2$. Perfusion is maintained by a peristaltic pump at a flow rate of 10 ml/min and perfusion pressure is monitored by a P23AA Statham pressure transducer attached to a side arm of the aortic inflow cannula and recorded on a Hewlett Packard 7702B recorder. The complete perfusion system is maintained within a thermostatically controlled plexiglass chamber maintained at 37° C.

The hearts are perfused 3–4 minutes to remove blood. After a 20 minute control period, global ischemia is initiated by stopping the pump and turning off the 95% $O_2$–5% $CO_2$. At the end of the ischemic period, the pump is restarted and the buffer reoxygenated.

Enzyme leakage from the heart cells is determined in effluent samples collected from the heart at specific time periods during the control period and during reperfusion. Lactate dehydrogenase (LDH) activity is assayed by monitoring the oxidation of NADH, using pyruvate as the substrate. NADH is monitored at 340 nm using a Perkin Elmer Lambda 3 recording spectrophotometer. As shown in FIG. 1, LDH activity from hearts treated with 10 μg TNF compared to controls indicates that the TNF protected the heart from damage mediated by its ischemia and reperfusion.

We claim:

1. A method for the protection of ischemic tissues, comprising the administration to said tissue prior to reperfusion of an effective amount of a tumor necrosis factor.

2. The method of claim 1, wherein said tumor necrosis factor is administered prior to or after removal of said tissue from a donor.

3. The method of claim 1, wherein said tumor necrosis factor is administered prior to or after transfer of said tissue to a patient.

4. The method of claim 1, wherein said tissue has been or is to be removed from a mammalian donor and transferred into a mammalian patient.

5. The method of claim 1, wherein said tissue is mammalian.

6. The method of claim 1, wherein said tumor necrosis factor is administered along with alpha, beta, or gamma-interferon.

7. The method of claim 1, wherein approximately 1–250 μg/m² of said tumor necrosis factor is administered.

8. The method of claim 1, wherein said tumor necrosis factor is tumor necrosis factor-α or tumor necrosis factor-β.

9. The method of claim 1, wherein said tumor necrosis factor is perfused into said tissue by mechanical means.

10. The method of claim 1, wherein said tumor necrosis factor is continuously perfused through said tissue with a pharmaceutically acceptable excipient.

11. The method of claim 10, wherein said tumor necrosis factor is perfused into said tissue before or after the tissue has been removed from a donor but prior to the implantation of said tissue into a patient, and wherein said tumor necrosis factor is replaced by an isotonic perfusion fluid free of tumor necrosis factor immediately prior to implantation of the tissue into said patient.

12. The method of claim 1, wherein said tumor necrosis factor is administered along with an antioxidant or fibrinolytic agent.

13. A method for the protection of ischemic tissue to be removed from a donor and transferred to a patient, comprising the administration to said donor prior to the removal of said tissue of an effective amount of a tumor necrosis factor.

14. The method of claim 13, wherein said donor and said patient are mammalian.

15. The method of claim 13, wherein said tumor necrosis factor is administered along with alpha, beta, or gamma-interferon.

16. The method of claim 13, wherein approximately 1–250 μg/m² of said tumor necrosis factor is administered.

17. The method of claim 13, wherein said tumor necrosis factor is tumor necrosis factor-α or tumor necrosis factor-β.

18. The method of claim 13, wherein said tumor necrosis factor is administered to said donor intravenously.

19. The method of claim 13, wherein said tumor necrosis factor is administered along with an antioxidant or fibrinolytic agent.

20. The method of claim 1, wherein said tissue is selected from the group consisting of muscle tissue, connective tissue, epithelial tissue, nervous tissue, vascular tissue, brain, reproductive organs, respiratory organs, digestive organs, excretory organs, urinary organs, sensory organs, and skeletal muscle organs.

21. The method of claim 13, wherein said tissue is selected from the group consisting of muscle tissue, connective tissue, epithelial tissue, nervous tissue, vascular tissue, brain, reproductive organs, respiratory organs, digestive organs, excretory organs, urinary organs, sensory organs, and skeletal muscle organs.

* * * * *

UNITED STATES PATENT AND TRADEMARK OFFICE
CERTIFICATE OF CORRECTION

PATENT NO. : 5,200,176
DATED : APRIL 6, 1993
INVENTOR(S) : WONG ET AL.

It is certified that error appears in the above-identified patent and that said Letters Patent is hereby corrected as shown below:

On the title page, Item [54] and Column 1, line 2, of invention:
"NEROSIS" should read --NECROSIS--.

Signed and Sealed this

First Day of June, 1999

Attest:

Q. TODD DICKINSON

*Attesting Officer*    *Acting Commissioner of Patents and Trademarks*